United States Patent [19]
Roy et al.

[11] Patent Number: 5,633,132
[45] Date of Patent: May 27, 1997

[54] DETERMINATION OF THE PRESENCE OF AN ANTIGEN, PARTICULARLY HLA-B27 ANTIGEN, AT THE SURFACE OF A CELL, PARTICULARLY LYMPHOCYTES, BY CYTOTOXICITY TEST COMBINED WITH FLUORESCENT STAINING

[75] Inventors: Raynald Roy, Ste-Foy; Jacques Hebert, Cap-Rouge, both of Canada

[73] Assignee: Immunova Ltee, Quebec, Canada

[21] Appl. No.: 234,394

[22] Filed: Apr. 28, 1994

[51] Int. Cl.$^6$ .................................. G01N 33/554
[52] U.S. Cl. .................. 435/6; 435/7.2; 435/7.24; 436/519; 436/800; 436/821
[58] Field of Search .................. 435/6, 7.2, 7.24; 436/519, 800, 821

[56] References Cited

U.S. PATENT DOCUMENTS

| | | | |
|---|---|---|---|
| 4,314,026 | 2/1982 | Descamps-Latscha | 435/7 |
| 4,628,026 | 12/1986 | Gardell et al. | 435/7 |
| 5,314,805 | 5/1994 | Haugland et al. | 435/29 |
| 5,369,010 | 11/1994 | Nelson et al. | 435/7.24 |

FOREIGN PATENT DOCUMENTS

| | | |
|---|---|---|
| 0212824 | 3/1987 | European Pat. Off. |
| WO92/21030 | 11/1992 | WIPO |

OTHER PUBLICATIONS

Heller et al., "Evaluation of an Automated Method of Percent Reactive Antibody Determination", *Human Immunology*, 35(3):179–187 (Nov. 1992).

Shinohara et al., "The Usefulness of IL-2-activated Lymphocyte of HLA-typing", *Chemical Abstracts*, 120(3), Abstract No. 28806n (1994) (no month is cited on copy of the reference).

Tanke et al., "Alternative Fluorochromes to Ethidium Bromide for Automated Read Out of Cytotoxicity Tests", *Journal of Immunological Methods*, 52:91–96 (1982) (no month is cited on copy of the reference).

J. Albrecht et al, Clinical Chemistry, 33, 1619–1623, 1987.

J. W. Bruning et al, Human Immunology, 5, 225–231, 1982.

C. Darke et al, In P. Dyer et al (Eds). *Histocompatibility Testing: A Practical Approach*, Oxford University Press, 1993, pp. 51–80.

"Procedures for HLA Determination" In *HLA–System* (1st English Ed.). Johannsen, R. and Teuter, Chr. (Eds.). (West Germany) pp. 44–65.

Kellner, H. and Yu, D. 91992). Rheumatol. Int. 12:121–127.

Kissmeyer–Nielsen, F. and Dick, H.M. (1979). "Lymphocytotoxicity Testing" In *Histocompatibility Techniques*. Elsevier/North–Holland Biomedical Press. pp. 9–50.

Loken, M. (1990) "Immunofluorescence Techniques" In *Flow Cytometry and Sorting* (2nd Ed). Melamed, M.R. et al. (Eds.) (Wiley–Liss, New York) pp: 341–353.

Pei, R. et al. (1993). Tissue Antigens. 41:200–203.

Sullivan, K.A. and Amos, D.B. (1986). "The HLA System and Its Detection". In *Manual of Clinical Laboratory Immunology* (3rd Ed.). Am Soc. Microbiol. pp. 835–846.

HLA–B27 Screening Kit For In Vitro Diagnostic Use. Becton Dickinson. Catalog No. 340183.

HLA–B27 Antigen Typing Kit Immunofluorescent Antibody Test In Vitro Diagnostic Use Only. Genetic Systems. Product No. 0710–10.

HLA–B27 Fluorescein Isothiocyanate (FITC) Conjugated Monoclonal Antibody. One Lambda Catalogue #B27F.

*Primary Examiner*—David Saunders
*Attorney, Agent, or Firm*—Merchant, Gould, Smith, Edell, Welter & Schmidt

[57] ABSTRACT

The present invention relates to a method of determining the presence of an antigen, particularly the HLA-$B_{27}$ antigen, at the surface of cells, particularly lymphocytes, by combining the sensitivity of a cytotoxicity test, particularly a lymphotoxicity test, combined to a fluororescence detection, particularly, by using propidium iodide. The claimed method does not involve any purification of lymphocytes from a blood sample. The erythrocytes contained in the test blood sample are lysed after the immune reaction and complement action is completed. Moreover, the formation of the immune complexes, the complement fixation and reaction and the staining of the cells may take place at the same time in the test tube. This method is therefore very simple and very fast to execute. The facility of reading the positive cells is also an advantage to the claimed method over and above the methods using dyes like eosin or trypan blue, because of the direct visualization of colored cells as positive cells. Another advantage of the claimed method resides in its versatility of reading. Quantitation and identification of the positive cells is rendered feasible by fluorescence microscopy as well as by flow cytofluorometry. The claimed method has been validated in the diagnosis of ankylosing spondylitis (AS) and reactive arthritis (RA) by typing lymphocytes HLA-$B_{27}$.

23 Claims, 2 Drawing Sheets

Positive control or Presence of HLA-B27

Negative control or Absence of HLA-B27

DETERMINATION OF THE PRESENCE OF AN ANTIGEN, PARTICULARLY HLA-B27 ANTIGEN, AT THE SURFACE OF A CELL, PARTICULARLY LYMPHOCYTES, BY CYTOTOXICITY TEST COMBINED WITH FLUORESCENT STAINING

BACKGROUND OF THE INVENTION

The determination of the presence of an antigen at the surface of a cell by immunofluorescence is a well-known technique. Usually, such determination involves the use of antibodies of polyclonal or monoclonal origin which bind specifically to this antigen. The presence of this antigen is revealed directly by the antibody which has been labelled with a fluorescent tag, or indirectly by reacting a second antibody which binds the first antibody, this second antibody bearing the immunofluorescent tag. These well-known procedures might be simple to execute at the expense of a high level of sensitivity.

A more sensitive approach involves the use of complement in cytotoxicity tests, the complement having this particularity to bind the constant fragment (Fc) of an antibody, and to create pores in the cells bearing the immune complex. When the target cells are lymphocytes, this test is called lymphotoxicity test. Lymphotoxicity tests usually need purified lymphocytes to insure an enrichment of the preparation to be analyzed and/or to get rid of other cells, particularly of erythrocytes, which could be identified as lymphocytes, and counted as such.

Preparations of purified lymphocytes can be obtained after more or less laborious procedures, which implies that a good level of sensitivity is gained at the expense of the simplicity and rapidity of execution.

There is clearly a need for a method of typing lymphocytes, which would reconcile good sensitivity as well as rapidity of testing.

The human leucocyte antigen (HLA) system is now known as the major histocompatibility complex (MHC). The highly polymorphic genes of this complex encode proteins, that are commonly referred to as MHC molecules or HLA antigens. Expressed on the surface of a variety of cells, these proteins are the principal determinants of graft rejection. Also, they have a major role in immune response and serve as genetic markers associated with disease susceptibility.

One of the most important associations known is certainly the HLA-$B_{27}$ with ankylosing spondylitis (AS) and reactive arthritis (RA). More than 95% of patients with AS and approximately 70% of the patients with RA bear HLA-$B_{27}$ antigen. The prevalence of this gene product is around 7% in normal Caucasian, 7% in Chinese, 6% in Mexican, 4% in American black and 0.8% in Japanese populations. The HLA-$B_{27}$ determination by a simple method could find a diagnostic use in conjunction with a clinical and radiological evidences.

Up to now, the most commonly known and used methods to evaluate the HLA-$B_{27}$ determinant are classified in two categories.

The first category regroups plate tests sold by the following companies: Gen Track Inc., 5100, Campus Drive, Plymouth Meeting, Pa. 19462; One lambda Inc., 21001, Kittridge St., Canoga Park, Calif. 91303-2801; and Laboratoire Omega Ltée, 11177, Hamon, Montréal (Québec), H3M 3E4. These tests are performed using plates coated with polyclonal antibodies and to which is added a test sample after purification of its leucocytes, and using the following general method:

isolating of lymphocytes on a Ficoll gradient, mixing the lymphocytes with antiserum contained in test plates, allowing for immune complexes to be formed during about 30 minutes, adding complement to these immune complexes and incubating for about 60 minutes, fixing and staining the lymphocytes with formaldehyde and eosin or trypan blue, and reading the results under an inverted phase-contrast microscope in the case eosin was used as a staining agent or under a microscope without phase contrast in the case trypan blue was used as a dye.

Whatever dye is used, the lysed cells (positive results) are dark and swollen while the negative cells are well-stained and retain their morphological characteristics. When the rate of lysis is at least 30% higher than in negative control, the result is assessed positive.

The second category regroups diagnostic kits containing monoclonal antibodies sold by the following companies: Becton Dickinson, 2350, Qume Drive, San Jose, Calif. 95131-1807; and One Lambda (address given above), and involves classical immunofluorescence procedure. The antibody is a monoclonal antibody which has been labelled with a fluorochrome. Laborious preparation of the lymphocytes to type might be rendered necessary because any cell susceptible to bind the labelled Fc fragment, like macrophages, monocytes, neutrophils, B cells and natural killer cells, must be eliminated from the preparation before the latter is reacted with these antibodies, in order to avoid false positive results. The identification and numbering of positive cells are made by flow cytometry, which means that the accessibility of this typing is reduced to the institutions which possess such a costly apparatus. Furthermore, the test can be performed by a highly skilled technician trained to operate this apparatus. Moreover, the interpretation of the results is rendered difficult by the absence of easy-to-interpret negative and positive controls. This test is not suitable for direct visualization under fluorescence microscopy unless the population of cells to test is very rich in antigens.

Therefore, there is clearly a need for a simple and sensitive procedure which would be available to any small laboratory simply possessing facilities and apparatus like a low-speed centrifuge and a fluorescence microscope. The use of a fluorochrome like propidium iodide which is commonly used to stain cell DNA might be advantageously used instead of dyes like eosin and trypan blue, for a direct evaluation of the positive cells.

STATEMENT OF THE INVENTION

The present invention relates to a method of determining the presence of an antigen, particularly the HLA-$B_{27}$ antigen, at the surface of cells, particularly lymphocytes, by combining the sensitivity of a cytotoxicity test, particularly a lymphotoxicity test, combined to a fluorochrome, particularly, propidium iodide.

The claimed method does not involve any purification of lymphocytes from a blood sample. The erythrocytes contained in the test blood sample are lysed after the immune reaction and complement action is completed. Moreover, the formation of the immune complexes, the complement fixation and reaction and the staining of the cells take place at the same time in the test tube. This method is therefore very simple and very fast to execute.

The complement fixation insures the sensitivity and the accuracy of this method. Even on cell population with low concentration of antigen at their surface, the complement binds to the Fc fragment of the bound antibody, creates pores on the membrane and allows the propidium iodide to enter the cell. This fluorochrome strongly binds the DNA of the cell and reveals this way the cell bearing this antigen. If any other cell contains receptors for the Fc fragment, the latter is no longer available to fix the complement and, consequently, as no damage is created to this cell by the fixation of the complement, no fluorochrome can enter this cell. This kind of cell remains negative. On the other hand, erythrocytes being anucleated cells, if any of those escape the lysis step, their coloration is fainter than the one of lymphocytes.

The facility of reading the positive cells is also an advantage to the claimed method over and above the methods using dyes like eosin or trypan blue. It is much easier to visualize colored cells as positive cells than to visualized colored cells as negative cells.

Another advantage of the claimed method resides in its versatility of reading. Quantitation and identification of the positive cells is rendered feasible by fluorescence microscopy as well as by flow cytofluorometry. The advantage of the latter is the obtention of the quantification of the fluorescent signal. However, for a simple diagnostic purpose, the present invention allows for a much greater availability of the test to laboratories or clinics which do not benefit of very costly and sophisticated equipment. Corollarily, the method can be performed and the results read by persons having an average skill in the field.

The claimed method has been validated in the diagnosis of SA and RA by typing lymphocytes HLA-$B_{27}$. Therefore, another object of the present invention is a diagnostic method and kit using a monoclonal antibody directed against the HLA $B_{27}$ antigen.

Finally, the claimed method, even though specifically practised for the diagnosis of SA and AR by determining the presence of HLA $B_{27}$ antigen, is considered as a general method applicable to various kinds of antigens present at the surface of cells. The general principles thereof will apply:

the simultaneity of the reactions antibody-antigen, fixation of the complement and staining of the positive cells, the combination of cytotoxicity test with fluorescent staining, and no purification of the target cell necessary as far as blood cell population is considered.

DESCRIPTION OF THE INVENTION

The claimed method is based on complement-dependent cytotoxicity assay which is a standard method that is routinely performed in clinical laboratories. After binding with an antibody directed against an antigen of interest, the cell membranes are disrupted by the cytotoxic effect of complement fixation. The specific case of the antigen HLA-$B_{27}$ which is present at the surface of patients' lymphocytes and which specifically binds to a monoclonal antibody called anti-HLA-$B_{27}$ antibody is hereinbelow illustrated by way of the following specific embodiments and Figures, and should not be regarded as limiting the scope of this invention:

Figure 1A:
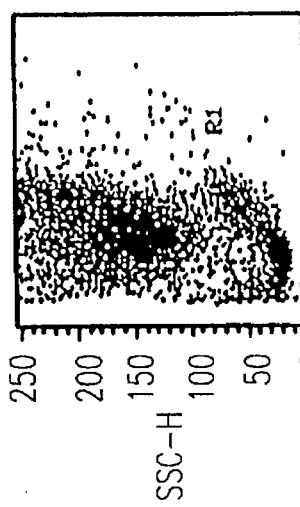
FIGS. 1a, 1b and 1c represent a flow cytometry analysis of a blood sample reacted with an anti-HLA $B_{27}$ antibody according to this invention (FIG. 1c), in comparison with positive and negative controls (C+ and C-, respectively).
Figure 1B:
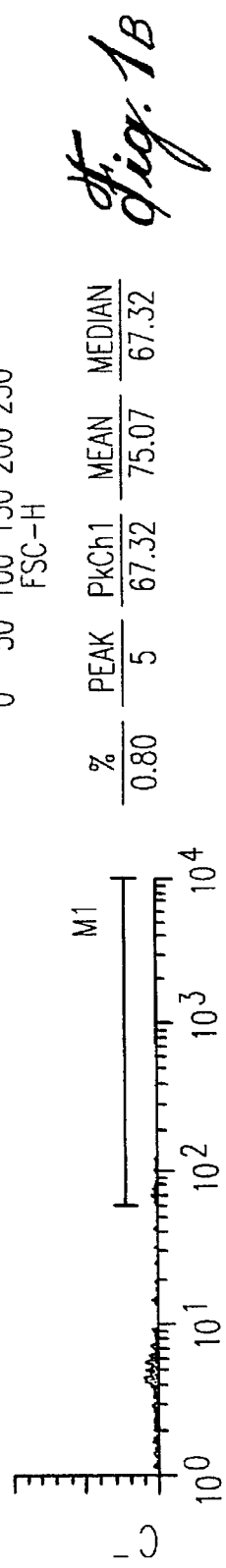
Figure 1C:
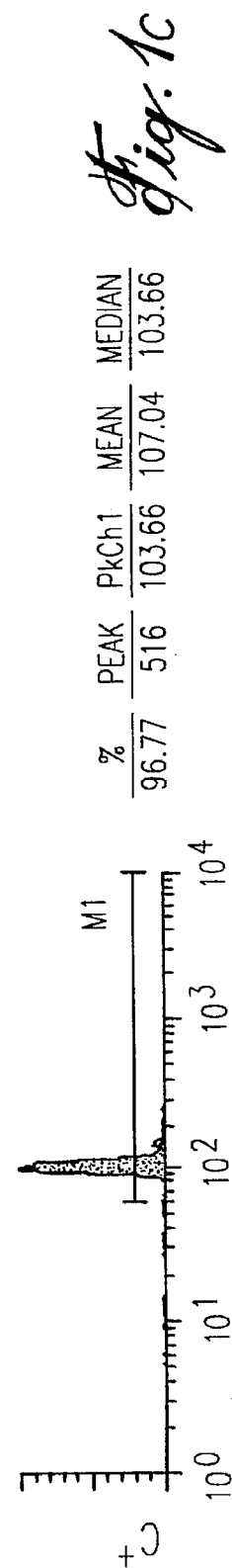
Figure 1D:
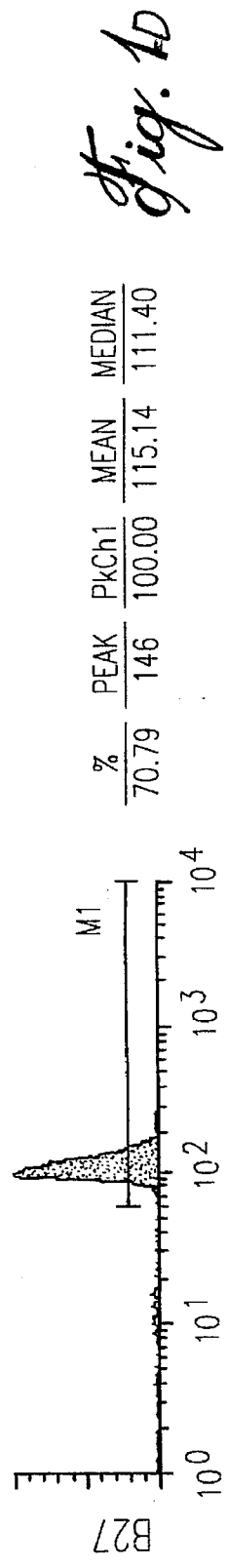

An immunofluorescence technique is used to identify the damaged cells which are identified following the penetration of a dye fluorescent reagent into the cell. The results are measured or read by either microscopy or flow cytometry. The dye fluorescent reagent should exclusively bind to intra-cellular components to avoid non-specific reactions. It should be understood that other dyes than fluorescent ones might be used in this method as far as they bind to intracellular components and inasmuch the coloration or signal provided for by this binding is detected, visualized and/or measured by appropriate means. A dye fluorescent reagent like propidium iodide is a candidate of choice because it strongly binds nucleic acids. Fluorescent reagents have, up to date, the advantage of providing for a signal which insures quantitative as well as qualitative analysis. Therefore, the versatility of the type of analysis to be performed insures a greater availability of the claimed method to many laboratories, this notwithstanding the degree of sophistication of the equipment and of level of skill of the staff habilitated perform this method and to interpret the results.

When this method is applied to the typing of lymphocytes, particularly to HLA-B27 typing, no purification thereof is necessary. Whole blood sample is collected in heparin or EDTA to avoid coagulation, and stored at room temperature. For optimal results, this sample of blood should be used with 24 hours after venipuncture. Refrigeration of blood samples must be avoided because it might give aberrant results.

When processed, three aliquots of blood are transferred into polystyrene test tubes identified C+, C- and test, which stands for positive control, negative control and test sample, respectively. Blood is diluted 40 times with phosphate buffer saline (PBS) to avoid inhibition of complement fixation by blood constituents or by the added anti-coagulants. The tubes are centrifuged at a low speed (200×g). Without disturbing the cell pellet, the is removed and discarded. Into the corresponding tube, the appropriate reagents are added. Reagents identified C+, C- and test might be conveniently provided in a dried form in a diagnostic kit, which kit is individually constructed for a particular purpose. A HLA-$B_{27}$ diagnostic kit will be exemplified hereinbelow.

In a kit, reagents must be kept frozen until use. Immediately before using, they are reconstituted in a suitable volume of cold distilled water and kept between 2° and 8° C.

| | Quantity |
|---|---|
| Reagent C+ contains: | |
| Monoclonal anti HLA class I (HR-32), which recognizes a "public" epitope, e.g. expressed in all cells bearing HLA class I molecules Provided by: Hébert J. and Roy, R. Québec | 1 part |
| Low Tox Rabbit Complement Provided by: Cedarlane 5516 - 8th Line, R.R. 2 Hornby, Ontario, Canada L0P 1E0 | 5 parts |
| Propidium Iodide Provided by: Aldrich 100 West St. Paul Ave Milwaukee, WI 53233 | 1 part |
| PBS + 7% BSA Provided by: Sigma | 3 parts |

| | Quantity |
|---|---|
| PO Box 14508, St. Louis MO 63178 Reagent C– contains: | |
| Low Tox Rabbit Complement Provided by: Cedarlane | 5 parts |
| Propidium Iodide Provided by: Aldrich | 1 part |
| PBS + 7% BSA Provided by: Sigma Reagent test contains: | 3 parts |
| Monoclonal anti HLA $B_{27}$ (HR-172) in 2% BSA Provided by: Hébert J. and Roy, R. Québec | 1 part |
| Low Tox Rabbit Complement Provided by: Cedarlane | 5 parts |
| Propidium Iodide Provided by: Aldrich | 1 part |

Blood and reagents are gently mixed and incubated for 60 minutes at room temperature in the dark.

To stop the reaction, the same volume of PBS as above is added, and the tubes are centrifuged at the same speed for the same duration of time. Again, the supernatant is carefully removed and discarded. The tubes are swirled or flicked to resuspend the cells in the residual volume.

Red cells are lysed with the aid of "whole blood lysing reagents" HLA-$B_{27}$ Lysing Solution (purchased from Becton Dickinson, 2350 Qume Drive, San Jose, Calif. 95131-1807) or Whole Blood Lysing Reagents (purchased from Coulter, P.O. Box 169015, Miami, Fla. 33116-9015), in accordance with the manufacturer's directions.

The results can be read in flow cytometry after resuspension in a suitable volume of PBS, or in microscopy after adding a mounting medium and pouring a drop of the mixture on a slide with a coverslip. The mounting medium has the following composition: glycine buffer 40%-glycerol 60%. Glycine buffer is made pH 8.6 and is composed as following: glycine 0.2M, sodium hydroxide 17.5 mM, sodium chloride 0.29M and sodium azide 15 mM. The mounting medium may be stored at room temperature.

Flow cytometry:

Samples are analyzed with a flow cytometer. Red fluorescence is measured with laser excitation at 488 nm and emission at 610 nm. Data acquisition of events are gated on forward scatter light parameter adjusted on lymphocytes. Debris must be eliminated by increasing the forward scatter threshold (cell number versus fluorescence intensity). Fluorescence signals are collected in log mode. An example of flow cytometry analysis is shown in FIG. 1.

Positive reaction will be represented by a clear fluorescence mean channel shift with positive control ($C^-$;, FIG. 2b) or test sample ($B^{27}$;, FIG. 2c) over negative control ($C^-$, FIG. 1a).

For a test to be considered valid, the positive control or the negative control must give appropriate reaction as defined by the criteria of flow cytometry analysis as already described. Failure of correct positive or negative control reactions means that the test result is invalid, and the whole procedure must be repeated.

Microscopy:

Samples are analyzed using a fluorescence microscope with a filter system for propidium iodide, using a maximum excitation wavelength of 490 nm and an emission wavelength of 620 nm.

The interpretation in microscopy will always refer to the positive and negative controls. Positive cells, which are morphologically regular, will present a red fluorescence. Negative control will show few or no colored cells.

Red fluorescent cells in the test sample will be considered as a positive result if the number thereof is 10% higher than in the negative control.

Figure 2A:
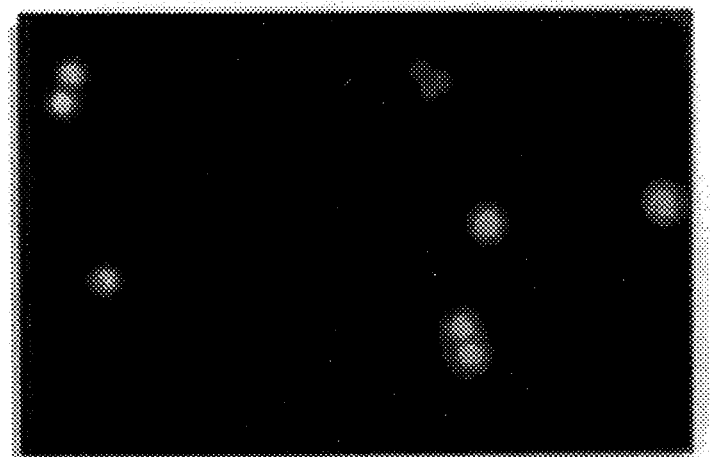
FIGS. 2a and 2b represent typical photographs of a positive HLA-$B_{27}$ blood sample or positive control (FIG. 2a) versus a negative HLA-$B_{27}$ blood sample or negative control (FIG. 2b), both revealed by the claimed method.
Figure 2B:

A typical picture of positive control or positive test sample is given for comparison with a negative control or negative test sample in FIG. 2 a) and b), respectively.

Limitations (mainly encountered in flow cytometry):

Refrigerated samples might give aberrant results.

Samples containing altered or very low lymphocyte counts might present problems.

Erroneous results might be obtained if the laser is misaligned or if the gates are improperly set.

If the red blood cells are not properly lysed, false results could be obtained because red blood cells are counted as lymphocytes.

As far as $B_{27}$ typing is concerned, $B_{47}$ phenotype (0.2% occurrence in Caucasian population) could present a false positive reaction due to its possible cross-reactivity).

This invention has been disclosed hereinabove, and it is understood that modifications could be brought to the described and claimed method without departing from the teachings of this disclosure. These modifications are therefore considered under the scope of this invention.

The embodiments of the invention in which an exclusive property or privilege is claimed are defined as follows:

1. A method of detecting the presence of an antigen at the surface of the cell membrane of cells contained in a test sample, which comprises the following steps:

(a) placing said cells in the presence of an antibody which specifically binds said antigen;

(b) allowing immune complexes to be formed between said antigen and antibody;

(c) placing said immune complexes in the presence of complement;

(d) allowing the constant region of the antibody of said immune complexes to fix the complement this fixation leading to the disruption of said cell membrane;

(e) placing said cells, the cell membrane of which is disrupted in the presence of a dye reagent which specifically binds intra-cellular components;

steps (a) to (e) being simultaneous; and (f) detecting the presence of dyed cells as an indication of the presence of said antigen at the surface of their cell membrane.

2. A method according to claim 1, wherein said antibody is a monoclonal antibody.

3. A method according to claim 1, wherein said intra-cellular components are nucleic acids.

4. A method according to claim 3, wherein said dye reagent is a fluorescent dye reagent.

5. A method according to claim 4, wherein said fluorescent dye reagent is propidium iodide.

6. A method according to claim 4, wherein the detecting step f) is made by flow cytometry.

7. A method according to claim 4, wherein the detecting step f) is made by fluorescence microscopy.

8. A method according to claim 1, wherein said test sample is whole anti-coagulated blood.

9. A method according to claim 8, wherein said cells are lymphocytes.

10. A method according to claim 9, wherein said antigen is a HLA determinant.

11. A method according to claim 10, wherein said HLA determinant is HLA-$B_{27}$ antigen.

12. A method according to claim 11, wherein said antibody is a monoclonal anti-HLA-$B_{27}$ antibody.

13. A method according to claim 10, wherein between steps (e) and (f), a step of lysing erythrocytes contained in said test sample is inserted.

14. A method according to claim 13, wherein said intracellular components are nucleic acids.

15. A method according to claim 14, wherein said dye reagent is a fluorescent dye reagent.

16. A method according to claim 15, wherein said fluorescent dye reagent is propidium iodide.

17. A method according to claim 15, wherein the detecting step f) is made by flow cytometry.

18. A method according to claim 15, wherein the detecting step f) is made by fluorescence microscopy.

19. A method for typing a HLA determinant beared at the surface of lymphocytes in a whole anticoagulated blood test sample, which comprises the following steps;
   (a) placing said blood test sample in the presence of an antibody which specifically binds said HLA determinant;
   (b) allowing immune complexes to be formed between said HLA determinant and antibody;
   (c) placing said immune complexes in the presence of complement;
   (d) allowing the of said immune complexes constant region of the antibody to fix the complement this fixation leading to the disruption of said lymphocyte cell membrane;
   (e) placing said cells, the cell membrane of which is disrupted in the presence of a fluorescent dye reagent which specifically binds intra-cellular components;
   steps (a) to (e) being simultaneous;
   (f) lysing erythrocytes contained in said blood test sample; and
   (g) detecting the presence of dyed lymphocytes as an indication of the presence of said HLA determinant at the surface of their cell membrane.

20. A method according to claim 19, wherein said HLA determinant is HLA-$B_{27}$ antigen.

21. A method according to claim 20, wherein said fluorescent dye reagent is propidium iodide.

22. A method for detecting the presence of antigens of interest at the surface of the cell membrane of a cell population contained in a test sample, which comprises the following steps:
   (a) distributing a substantially equal amount of cells in three test tubes $C^+$, test and $C^-$;
   (b) adding to tubes $C^+$ and test a suitable amount of a first antibody and of a second antibody, respectively, said first antibody specifically binding an epitope which is common to all cells of said cell population, and said second antibody specifically binding an epitope which is essentially unique to said antigen of interest;
   (c) allowing immune complexes to be formed between said epitopes and antibodies;
   (d) adding complement to tubes $C^+$, test and $C^-$;
   (e) allowing the constant region of said antibodies to fix the complement in tubes $C^+$ and test; allowing the cells of tube $C^-$ to fix the complement, wherein fixation by non-specific components is measured; the fixation of the complement leading to the destruction of the cell membrane of the cells bearing said epitopes or non-specific components;
   (f) adding to tubes $C^+$, test and $C^-$ a fluorescent dye reagent which specifically binds intra cellular components;
   the steps of (a) to (f) being simultaneous;
   (g) detecting the number of dyed cells in tubes $C^+$, test and $C^-$ to obtain values $C^+$, test and $C^-$, respectively; and,
   (h) calculating the percentage value of (test—$C^-$)/$C^+\times$100; a percentage value (test—$C^-$)/$C^+\times$100 superior to 10% being an indication of the presence of said antigen of interest in said test sample.

23. A method for typing a HLA determinant borne at the surface of lymphocytes in a whole anti-coagulated test sample, which comprises the following steps:
   (a) distributing a substantially equal amount of blood cells in three test tubes $C^+$, test and $C^-$;
   (b) adding to tubes $C^+$ and test a suitable amount of a first antibody and of a second antibody, respectively, said first antibody specifically binding a HLA determinant which is common to all lymphocytes, and said second antibody specifically binding a HLA determinant which is essentially unique to a type of lymphocytes;
   (c) allowing immune complexes to be formed between said HLA determinants and antibodies;
   (d) adding complement to tubes $C^+$, test and $C^-$;
   (e) allowing the constant region of said antibodies to fix the complement in tubes $C^+$ and test; allowing the blood cells of tube $C^-$ to fix the complement, wherein fixation by non-specific components is measured; the fixation of the complement leading to the destruction of the cell membrane of the blood cells bearing said HLA determinants or non-specific components;
   (f) adding to tubes $C^+$, test and $C^-$ a fluorescent dye reagent which specifically binds intra-cellular components;
   the steps of (a) to (f) being simultaneous;
   (g) detecting the number of dyed lymphocytes and blood cells in tubes $C^+$, test and $C^-$ to obtain values $C^+$, test and $C^-$ respectively; and
   (h) calculating the percentage value of (test—$C^-$)/$C^+\times$100; a percent value (test—$C^-$)/$C^+\times$100 superior to 10% being an indication of the presence of said HLA determinant in said blood test sample.

* * * * *

UNITED STATES PATENT AND TRADEMARK OFFICE
CERTIFICATE OF CORRECTION

PATENT NO. : 5,633,132
DATED : MAY 27, 1997
INVENTOR(S) : ROY ET AL.

It is certified that error appears in the above-identified patent and that said Letters Patent is hereby corrected as shown below:

Col. 4, line 48: insert —For processing one part of blood,— after the words "2 and 8°C." (as a heading)

Col. 5, line 53: "($C^-$,)" should read —($C^-$;,—

Col. 6, line 41, claim 1: insert —,— after the word "complement"

Col. 7, line 28, claim 19: delete "of said immune complexes" after the word "the"

Col. 7, line 30, claim 19: insert —of said immune complexes— after the word "antibody"

Col. 7, line 30, claim 19: insert —,— after the word "complement"

Signed and Sealed this

Twenty-eighth Day of July, 1998

*Attest:*

*Attesting Officer*

BRUCE LEHMAN
*Commissioner of Patents and Trademarks*